United States Patent
Kahn et al.

(10) Patent No.: US 7,647,196 B2
(45) Date of Patent: Jan. 12, 2010

(54) HUMAN ACTIVITY MONITORING DEVICE WITH DISTANCE CALCULATION

(75) Inventors: Philippe Kahn, Aptos, CA (US); Arthur Kinsolving, Santa Cruz, CA (US); Mark Andrew Christensen, Santa Cruz, CA (US); Brian Y. Lee, Aptos, CA (US); David Vogel, Santa Cruz, CA (US); Paul Andrew Mietz Egli, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 0 days.

(21) Appl. No.: 11/891,112

(22) Filed: Aug. 8, 2007

(65) Prior Publication Data

US 2009/0043531 A1    Feb. 12, 2009

(51) Int. Cl.
   *G06F 3/00* (2006.01)
(52) U.S. Cl. .................. 702/149; 702/142; 702/150; 702/154
(58) Field of Classification Search .......... 702/127, 702/141, 150, 160, 173, 178; 73/510; 340/573.1; 705/2

See application file for complete search history.

(56) References Cited

U.S. PATENT DOCUMENTS

| | | | |
|---|---|---|---|
| 4,285,041 A | 8/1981 | Smith | |
| 4,578,769 A | 3/1986 | Frederick | |
| 5,446,725 A | 8/1995 | Ishiwatari | |
| 5,593,431 A | 1/1997 | Sheldon | |
| 5,955,667 A | 9/1999 | Fyfe | |
| 5,976,083 A | 11/1999 | Richardson et al. | |
| 6,135,951 A | 10/2000 | Richardson et al. | |
| 6,145,389 A | 11/2000 | Ebeling et al. | |
| 6,513,381 B2 * | 2/2003 | Fyfe et al. | 73/510 |
| 6,522,266 B1 | 2/2003 | Soehren et al. | |
| 6,532,419 B1 | 3/2003 | Begin et al. | |
| 6,539,336 B1 | 3/2003 | Vock et al. | |
| 6,790,178 B1 | 9/2004 | Mault et al. | |
| 6,813,582 B2 * | 11/2004 | Levi et al. | 702/141 |
| 6,823,036 B1 | 11/2004 | Chen | |
| 6,836,744 B1 * | 12/2004 | Asphahani et al. | 702/141 |
| 6,881,191 B2 | 4/2005 | Oakley et al. | |

(Continued)

OTHER PUBLICATIONS

Lee, Seon-Woo, et al., "Recognition of Walking Behaviors for Pedestrian Navigation," ATR Media Integration & Communications Research Laboratories, Kyoto, Japan, 4 pages.

(Continued)

*Primary Examiner*—Eliseo Ramos Feliciano
*Assistant Examiner*—Felix E Suarez
(74) *Attorney, Agent, or Firm*—Blakely, Sokoloff, Taylor & Zafman, LLP; Judith A. Szepesi

(57) ABSTRACT

A method of monitoring human activity includes monitoring accelerations using an inertial sensor disposed at one of a plurality of locations on a human body, wherein at least one of the plurality of locations is not a foot location. A plurality of steps are counted based on the accelerations. A gait characteristic of the plurality of steps is determined. The characteristic is used to determine a stride length. At least one of a distance traveled and a speed of travel are determined based on the stride length.

31 Claims, 10 Drawing Sheets

U.S. PATENT DOCUMENTS

| | | | |
|---|---|---|---|
| 6,885,971 | B2 | 4/2005 | Vock et al. |
| 6,898,550 | B1 | 5/2005 | Blackadar et al. |
| 6,941,239 | B2 * | 9/2005 | Unuma et al. ............ 702/141 |
| 6,959,259 | B2 | 10/2005 | Vock et al. |
| 7,072,789 | B2 | 7/2006 | Vock et al. |
| 7,092,846 | B2 | 8/2006 | Vock et al. |
| 7,148,797 | B2 | 12/2006 | Albert |
| 7,158,912 | B2 | 1/2007 | Vock et al. |
| 7,171,331 | B2 | 1/2007 | Vock et al. |
| 7,200,517 | B2 | 4/2007 | Darley et al. |
| 7,212,943 | B2 | 5/2007 | Aoshima et al. |
| 7,220,220 | B2 | 5/2007 | Stubbs et al. |
| 7,328,611 | B2 | 2/2008 | Klees et al. |
| 7,387,611 | B2 | 6/2008 | Inoue et al. |
| 2002/0109600 | A1 | 8/2002 | Mault et al. |
| 2002/0151810 | A1 | 10/2002 | Wong et al. |
| 2004/0225467 | A1 | 11/2004 | Vock et al. |
| 2005/0033200 | A1 | 2/2005 | Soehren et al. |
| 2005/0222801 | A1 | 10/2005 | Wulff et al. |
| 2005/0240375 | A1 | 10/2005 | Sugai |
| 2005/0248718 | A1 | 11/2005 | Howell et al. |
| 2006/0136173 | A1 | 6/2006 | Case et al. |
| 2006/0223547 | A1 | 10/2006 | Chin et al. |
| 2007/0063850 | A1 * | 3/2007 | Devaul et al. ............ 340/573.1 |
| 2007/0142715 | A1 | 6/2007 | Banet et al. |

OTHER PUBLICATIONS

Ormoneit, D., et al., "Learning and Tracking Cyclic Human Motion," 7 pages.

Dao, Ricardo, "Inclination Sensing with Thermal Accelerometers", MEMSIC, May 2002, 3 pages.

Mizell, David, "Using Gravity to Estimate Accelerometer Orientation", Seventh IEEE International Symposium on Wearable Computers, 2003, 2 pages.

Weinberg, Harvey, "MEMS Motion Sensors Boost Handset Reliability", Jun. 2006, http://www.mwrf.com/Articles/Print.cfm?ArticleID=12740, Feb. 21, 2007, 4 pages.

PCT International Search Report and Written Opinion for International Application No. PCT/US2008/072537, mailed Oct. 22, 2008, 10 pages.

PCT International Search Report and Written Opinion for PCT/US2009/48523, mailed Aug. 27, 2009, 8 pages.

Margaria, Rodolfo, "Biomechanics and Energetics of Muscular Exercise", Chapter 3, pp. 105-125, Oxford: Clarendon Press 1976.

* cited by examiner

US 7,647,196 B2

HUMAN ACTIVITY MONITORING DEVICE WITH DISTANCE CALCULATION

FIELD OF THE INVENTION

This invention relates to monitoring human activity, and more particularly to accurately measuring distance traveled for monitored human activity.

BACKGROUND

The development of Micro-Electro-Mechanical Systems (MEMS) technology has enabled manufacturers to produce inertial sensors (e.g., accelerometers) of sufficiently small size, cost, and power consumption to fit into portable electronic devices. Such inertial sensors can be found in a limited number of commercial electronic devices such as cellular phones, portable music players, pedometers, game controllers, and portable computers.

Step counting devices (e.g., pedometers) are used to monitor an individual's daily activity by keeping track of the number of steps that he or she takes. In general, step counting devices are clipped to a user's hip, and do not accurately count steps when placed elsewhere on a user's body.

Some step counting devices include an inertial sensor placed at specific locations on a user's body (e.g., in a user's shoe). Inertial sensors placed in a user's shoe (known as foot pods) may be used to determine a user's speed and distance because the foot comes to rest once for each step. However, conventional devices are not able to accurately determine distance and speed based on inertial sensors placed elsewhere on a user's body. Such conventional devices generally measure only a number of steps walked.

BRIEF DESCRIPTION OF THE DRAWINGS

The present invention is illustrated by way of example, and not by way of limitation, and can be more fully understood with reference to the following detailed description when considered in connection with the following figures.

DETAILED DESCRIPTION

Embodiments of the present invention are designed to monitor human activity using an inertial sensor. In one embodiment, accelerations are monitored from an inertial sensor disposed at one of multiple locations on a human body. Examples of locations at which the inertial sensor may be disposed include on the wrist, hip, chest, head, near the eyes, etc. Steps are counted based on the monitored accelerations from the inertial sensor. A gait characteristic of the steps is determined, which may be used to determine a stride length. In one embodiment, determining the stride length includes locating a stride length associated with the one or more gait characteristics in a data structure. At least one of a distance traveled and a speed of travel are determined based on the stride length.

To walk or run, an individual must lift a first leg, move it forward, plant it, and then repeat the same series of motions with a second leg. For a particular individual moving at a relatively steady speed, each of the series of walking and/or running motions will usually occur in about the same amount of time. The repeated set of motions can be considered a unit, and defines a motion cycle. The amount of time that it takes to complete one motion cycle defines a step period, and the number of motion cycles that occur in a given unit of time define a step cadence. Generally, an increased step cadence reflects a greater stride length.

Figure 1:
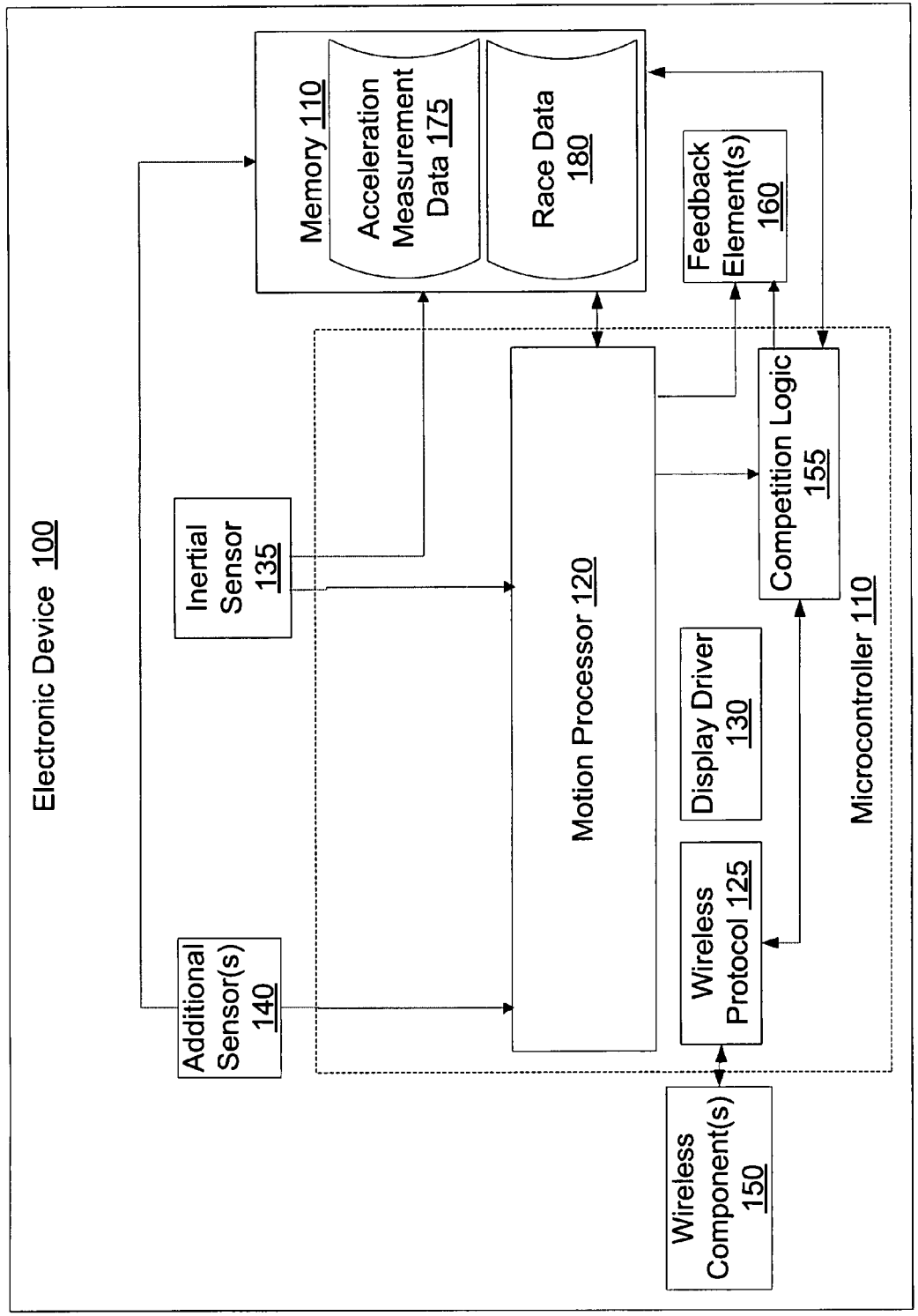
FIG. 1 is a block diagram illustrating an electronic device, in accordance with one embodiment of the present invention.

FIG. 1 is a block diagram illustrating an electronic device 100, in accordance with one embodiment of the present invention. In one embodiment, the electronic device 100 is a portable electronic device that includes one or more inertial sensors. Electronic device 100 may be a cellular phone, wrist watch, mp3 player, personal digital assistant (PDA), mobile game console, laptop computer, etc. The inertial sensors may measure accelerations along a single axis or multiple axes, and may measure linear as well as rotational (angular) accelerations. In a further embodiment, one or more inertial sensors together provide three dimensional acceleration measurement data.

The electronic device 100 may be used to identify whether a user is walking or running, and to count steps walked and/or run. In one embodiment, steps may be accurately counted, and speed and distance traveled may be accurately determined, regardless of the placement and/or orientation of the device 100 on a user. In a further embodiment, steps may be accurately counted, and speed and distance may be accurately determined, whether the electronic device 100 maintains a fixed orientation or changes orientation during use. In one embodiment, electronic device 100 operates in conjunction with additional devices (e.g., a server or mobile computing device) and/or sensors to count steps, determine speed of travel, determine distance traveled, etc.

The electronic device 100 in the embodiment shown in FIG. 1 comprises a motion processor 120, an inertial sensor 135, a memory 110, a wireless protocol 125 and one or more wireless components 150. The electronic device 100 may further comprise one or more additional sensors 140, competition logic 155, one or more feedback elements 160, and a display driver 130.

The inertial sensor 135 may generate acceleration measurement data 175 continuously, or at a sampling rate that may be fixed or variable. In one embodiment, the inertial sensor 135 receives a timing signal from a timer (not shown) to take measurements at the sampling rate. In one embodiment, the inertial sensor 135 is coupled to the motion processor 120, and acceleration measurement data 175 is sent to the motion processor 120 for processing. The acceleration measurement data 175 may be received by the motion processor 120 at a predetermined sampling rate, which may be fixed or variable. In one embodiment, the inertial sensor 135 is coupled to the memory 110, to store acceleration measurement data 175. In one embodiment, a buffer may collect acceleration measurement data 175, and the buffered data may be used by motion processor 120 for its calculations.

The motion processor 120 may process acceleration measurement data 175 to detect steps. In one embodiment, a series of motion criteria are applied to the acceleration measurement data 175 to detect steps. Motion criteria may include acceleration thresholds (e.g., a step may be counted if the measured acceleration is below a first threshold and/or above a second threshold), acceleration comparison requirements (e.g., a step may be counted if a current measurement of acceleration is above or below one or more previous measurements of acceleration), cadence windows (e.g., a step may be counted if accelerations characteristic of a step occur within a certain timeframe as measured from a previous step), etc. In one embodiment, the method described in co-pending U.S. patent application Ser. No. 11/644,455 entitled "Human Activity Monitoring Device" may be used to detect steps.

In one embodiment, if each of the motion criteria are satisfied, a step may be identified, and counted. Alternatively, if a sufficient number of the motion criteria are satisfied, a step may be counted. In one embodiment, a different set of motion criteria may apply for running and for walking. For example, a first threshold and first cadence window may be used to determine if a step has occurred while a user is running, and a second threshold and second cadence window may be used to determine if a step has occurred while a user is walking.

In one embodiment, the one or more additional sensors 140 also acquire data, and send the data to motion processor 120 memory 110 and/or buffer. The one or more additional sensors 140 may include a heart rate sensor such as an electrocardiograph (EKG or ECG). Heart rate measurement data gathered from the heart rate sensor may be combined with acceleration measurement data 175 by motion processor 120 to make determinations about the environment/terrain in which a user is walking or running. For example, if a user cadence remains steady or decreases, but a user heart rate increases, it may be inferred that the user has begun ascending a slope or stairs (going uphill). Once the heart rate measurement data is calibrated to cadence data for the user, a grade (incline) may be determined based on an interplay between the heart rate and the cadence. Therefore, for example, from a specific cadence and a specific heart rate, it may be determined that a user is going up an incline of between 2-3 degrees. Such calibration may be achieved, for example, by using a pressure sensor, or user input of distance ascended, as described further with reference to FIG. 2.

Additional sensors 140 may also include additional inertial sensors, a pressure sensor (e.g., altimeter), a moisture sensor, a capacitance sensor, a sound sensor (e.g., microphone), a heat sensor (e.g., thermometer, thermistor, etc.), global positioning system (GPS), or any other sensor capable of placement in a portable device. Such additional sensors may be used to determine additional information about a user's environment, terrain being traveled, a user's physical condition and/or health, etc. In one embodiment, the one or more additional sensors 140 take measurements at one or more set sampling rates that may be fixed or variable. In one embodiment, the set sampling rates are the same as the sampling rate at which the acceleration measurements are taken. Alternatively, one or more of the set sampling rates may vary from the sampling rate of the acceleration measurements.

In one embodiment, electronic device 100 includes one or more feedback elements 160. Feedback elements 160 may be internal to (e.g., a part of) or external to (e.g., not attached to) the electronic device 100. Feedback elements 160 may provide one or more of aural feedback (e.g., a buzz, beep, tune, spoken words, etc.), visual feedback (e.g., a blinking or solid light, number display, etc.) and tactile feedback (e.g., a vibration, movement, or slight shock). Feedback may be used, for example, to notify a user to speed up or to slow down, to notify a user that a specified period of time has elapsed, etc. In one embodiment, the type of user feedback, and when to provide user feedback, is user selectable. For example, a user may select to be given a notice to slow down when the user's heart rate exceeds an upper threshold, and to speed up when the user's heart rate falls below a lower threshold. In a further embodiment, user feedback may be application specific. For example, if a user is in a competition, specific feedback may be used to urge the user to speed up, to inform the user of his standing as compared to other competitors (e.g., whether a competitor is gaining on user, whether user is gaining on a competitor, etc.), and so on.

Multiple feedback conditions may be active concurrently. For example, a user may select to receive feedback if a running speed falls below a lower threshold and if a heart rate falls below a lower threshold. This enables a user to more accurately control workout intensity.

In one embodiment, the electronic device 100 includes a wireless protocol 125 and one or more wireless components 150. The wireless protocol 125 may be Bluetooth, Zigbee, infrared, radiofrequency (RF), personal area network (PAN), or any other wireless communication protocol. Alternatively, the electronic device 100 may include a wired protocol (not shown) such as firewire, universal serial bus (USB), etc. In one embodiment, the electronic device 100 includes both a wireless protocol 125 and a wired protocol. The wireless and/or wired protocol may enable the electronic device 100 to communicate with additional devices, such as a server, mobile device, personal computer, etc.

In one embodiment, the electronic device 100 includes a display driver 130. The display driver 130 may control a built-in display (not shown) of the electronic device, or an external display (not shown) that may be connected with the electronic device 100 via a wired or wireless connection.

Figure 2:
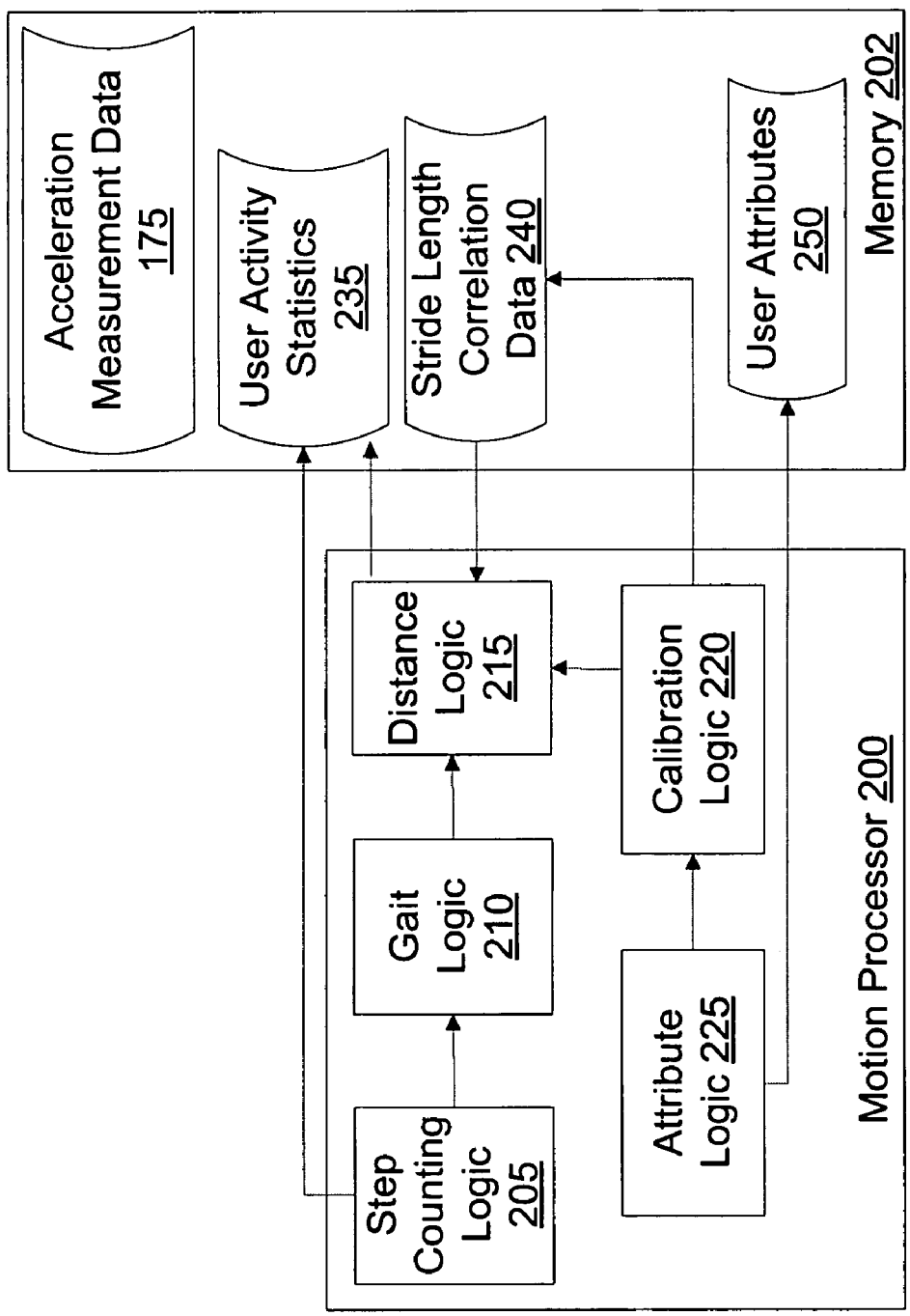
FIG. 2 is a block diagram illustrating a detailed view of a motion processor connected with a memory, in accordance with one embodiment of the present invention.

Memory 110 may include one or more of volatile memory (e.g., random access memory (RAM)), nonvolatile memory (e.g., read only memory (ROM), or flash memory), a hard disk drive, an optical drive, etc. Memory 110 may comprise multiple memories, i.e. a RAM memory used as a buffer, and a flash memory used to store other data. In one embodiment, memory 110 stores acceleration measurement data 175. In one embodiment, memory 110 stores race data 110. Memory 110 may also store one or more of user activity statistics, stride length correlation data, and user attributes, as shown in FIG. 2.

Some of the data may be converted to and/or stored in a specified format. In one embodiment, formats may include a generic format readable by multiple different computing devices. Examples of generic formats for the race data 180 include extensible markup language (XML) and standard generalized markup language (SGML).

Returning to FIG. 1, stored race data 180 may be speed and distance data that has been collected by another electronic device. Race data 180 is used to enable users to compete with each other in races while not being in the same place, nor running at the same time. The user's system, in one embodiment, receives other competitors' race data. The race data 180 may have been collected at a previous time, and transmitted to the memory 110 of electronic device 100 directly or through a server. Alternatively, the race data 180 may be received in real time from a different electronic device or from a server via wireless protocol 125.

In one embodiment, the electronic device 100 includes competition logic 155. The competition logic 155 receives performance data (e.g., distance, number of steps, speed, etc.) from motion processor 120, and compares the data to stored race data 180 from other competitors. Competition logic 155 may initiate and/or enable participation in a competition between users of different electronic devices. Competitions may include running competitions and walking competitions, examples which include fastest time for a given distance, furthest distance in a given amount of time, etc. A competition may occur in real time (in which users run or walk at the same time) or at different times (referred to as a time-shifted competition). For a time-shifted competition, a time limit may be determined, after which the competition may be completed, whether or not all competitors have finished competing.

Whether a competition is a real time competition or a time-shifted competition, competitors may compete from the same or different locations. For example, the race data 180 may have been collected as a first user ran at a first location, and the performance data may have been collected as a second user ran at a second location.

In one embodiment, race data 180 and/or current performance data may be normalized. In one embodiment, normalizing includes applying a correction factor to the race data 180 and/or the performance data. The correction factor may include, for example, adding an amount of time to a user's completion time, subtracting distance from a user's required distance to completion, etc. Race data 180 and performance data may be normalized based on a number of factors, such as incline, ambient temperature, altitude, age, athletic ability, etc. For example, if a first user ran on a 3 degree incline, and a second user ran on level ground, the normalization may result in effective time to completion being subtracted from the first user's performance data.

To determine whether and how to normalize based on incline, in one embodiment a pressure sensor may be used to detect an incline. Alternatively, a calibrated heart rate vs. cadence correlation may be used to determine how to normalize for incline. To determine how to normalize for ambient temperature, a thermometer may be used, and to determine how to normalize for altitude, a pressure sensor may be used. Other sensors may also be used to normalize for additional environmental variables.

In one embodiment, race data 180 and/or performance data may be normalized based on user age, athletic ability, and/or past performance. Such normalization may include applying a handicap (e.g., time or distance) to one or more of the competitors based on a difference between athletic ability levels and/or a difference between past performances of competitors. Accordingly, users of different levels of ability may remain competitive with one another and may run in virtual races.

Competition logic 155 may compare a user's current performance with the race data 180 in real time. Accordingly, race data 180 may be time shifted so that it is presented as though all competitors started the race at a single time. This provides feedback to the user, as in a real race, enabling him or her to know whether he is ahead or behind of other competitors. A user may then be notified that he needs to run faster to win, or that another competitor is catching up, for example, by feedback provided by the one or more feedback elements 160. Thus, the user may know his or her standing throughout the competition.

Where competition participants compete in real time (races at the same time), in one embodiment race data 180 may be wirelessly streamed between electronic devices of competitors. Streaming may occur via one or more servers, or may occur directly between electronic devices. Users may be continuously or periodically updated with a comparison of their performance to the performances of the other competitors during the competition.

Once a user has completed the competition, his or her race data 180 may be recorded and/or uploaded to a server or other electronic device or devices. If the competition is a time-shifted competition, other users may download the uploaded race data 180 to compete against it.

In one embodiment, users may compete against their own previous time as well. The race data 180 may represent the user's own past performance(s). This enables a user to train, and to see the improvement, and compete against himself.

In one embodiment, motion processor 120, display driver 130, wireless protocol 125 and competition logic 155 are logics executed by a microcontroller 105, field programmable gate array (FPGA), application specific integrated circuit (ASIC), or other dedicated processing unit. In another embodiment, one or more of the motion processor 120, display driver 130, wireless protocol 125 and competition logic 155 may be logics executed by a central processing unit. Alternatively, one or more of the motion processor 120, display driver 130, wireless protocol 125 and competition logic 155 may include a state machine (e.g., an internal logic that knows how to perform a sequence of operations), a logic circuit (e.g., a logic that goes through a sequence of events in time, or a logic whose output changes immediately upon a changed input), or a combination of a state machine and a logic circuit. In one embodiment, one or more of the elements described above may be part of a server, rather than part of an electronic device. In one embodiment, the electronic device may only include an inertial sensor and communications mechanism, with all calculations and processes performed on a remote device, such as a server.

FIG. 2 is a block diagram illustrating a detailed view of a motion processor 200 connected with a memory 202. In one embodiment, the motion processor 200 and the memory 202 correspond to the motion processor 120 and memory 110 of FIG. 1. The motion processor 200 may include a step counting logic 205, a gait logic 210, a distance logic 215, an attribute logic 225, and a calibration logic 220. The memory 202 may include acceleration measurement data 230, user activity statistics 235, stride length correlation data 240 and user attributes 250. In one embodiment, the memory 202 may be distributed across multiple memory elements and/or memory types. In one embodiment, memory 202 may include remote memory stored on a server or other remote device, as well as memory within the portable electronic device.

User activity statistics 235 may include multiple statistics associated with running and/or walking. Examples of user activity statistics include data about recent workouts, distance traveled per workout, distance traveled per day, average speed, highest speed, average incline of surface traveled, average heart rate, etc.

User attributes 250 may include user weight, height, age, gender, athletic ability, etc. User attributes may be used to calibrate stride length correlation data 240, calculate calorie expenditure, determine a user's maximum heart rate, etc. User attributes may be entered by a user, obtained from other sources, or determined automatically.

Stride length correlation data 240 may assign a specific stride length to a step based on gait characteristics associated with the step. Examples of gait characteristics include step cadence, heel strike, and other gait characteristics that can be derived from acceleration measurements. In one embodiment, the stride length correlation data 240 includes a stride length algorithm that identifies a specific stride length when one or more gait characteristics are used as an input. For example, if a step cadence of 70 steps per minute and a specific heel strike are detected, a stride length of 2 ft. may be determined. The stride length algorithm may vary depending on user attributes (e.g., depending on user weight, height, athletic ability, etc.).

In one embodiment, the stride length correlation data 240 includes a stride length data structure (e.g., a lookup table, tree, etc.) that has a collection of entries (e.g., 10 entries, 20 entries, 100 entries, etc.). Each entry may associate a specific set of gait characteristics with a specific stride length. For example, the data structure may include a first entry associating a cadence of 70 steps per minute with a stride length of 2.6 feet, a second entry associating a cadence of 100 steps per minute with a stride length of 3 feet, etc. Each entry in the data structure may be associated with a range of gait characteristics. Therefore, for example, the cadences of 5-10 steps per minute may all be associated with a stride length of 2 feet in an entry. The use of a data structure may require less computing power than the use of the algorithm. The greater the number of entries, the more accurate the data structure, but the more memory it may require.

A correlation between stride length and gait characteristics may differ depending on whether a user is walking or running. Accordingly, stride length correlation data 240 may include two different sets of correlation values: a first set for running, and a second set for walking. A first set of correlation values may include an algorithm or data structure for running, and a second set of correlation values may include an algorithm or data structure for walking. The walking data structure may have entries separated by smaller increments than the running data structure. For example, the walking data structure may have entries in tenth of a mile per hour increments, and the running data structure may have entries in fifth of a mile per hour increments. In one embodiment, each tenth of a mile per hour, ranging from 1 mph through 5 mph in one embodiment, may be associated with a specific stride length for walking, and each fifth of a mile per hour, ranging from 5 mph and up in one embodiment, may be associated with a specific stride length for running.

Step counting logic 205 may count steps based on acceleration measurement data 175 and/or data received from additional sensors. Steps may be counted regardless of an orientation of an inertial sensor that supplies the acceleration measurement data 175, and may be counted whether the inertial sensor retains a fixed orientation, or whether the inertial sensor changes orientation before, during, or after steps are measured. When a step is detected, it may be recorded as one of the user activity statistics 235 in the memory 110. One embodiment of a method for counting steps may be found in co-pending application U.S. Ser. No. 11/644,455, entitled "Human Activity Monitoring Device.". Alternative means of counting steps may be used.

In one embodiment, the gait logic 210 is connected with step counting logic 205 to receive a step notice when a step is detected. When step counting logic 205 notifies gait logic 210 that a step has occurred, gait logic 210 may analyze acceleration measurement data 175 from which the step was identified. Based on the analysis of the acceleration measurement data 175, gait logic 210 may determine one or more gait characteristics associated with the step.

Distance logic 215 may be connected with gait logic 210, and may receive the step notice and the gait characteristics associated with the step. Distance logic 215 may compare the gait characteristics to stride length correlation data 240 stored in memory 115. In one embodiment, comparing the gait characteristics to the stride length correlation data 240 includes using the gait characteristics as inputs to a stride length algorithm. In another embodiment, comparing the gait characteristics to the stride length correlation data 240 includes locating an entry in a stride length data structure to determine a stride length associated with the located entry. Based on the comparison, distance logic 215 may determine a distance traveled by the step. In one embodiment, distance logic averages gait characteristics for a number of steps (e.g., 2 steps, 4 steps, etc.) and uses the average gait characteristics to determine stride length. Stride lengths of multiple steps are combined to determine a distance traveled.

In one embodiment, distance logic 215 receives additional sensor data from one or more additional sensors. Distance logic 215 may analyze the additional sensor data to determine information about the stride lengths and/or distance traveled. For example, distance logic 215 may receive heart rate data from a heart rate sensor, and may use the heart rate data (e.g., by applying a heart rate vs. cadence correlation) to determine whether the distance includes a positive or negative incline.

In one embodiment, the additional sensor data is used to adjust a stride length to gait characteristic correlation (as determined using the stride length correlation data 240) as characteristics of the distance traveled change. For example, a user's stride length may differ between walking on a level surface, walking uphill, and walking downhill. When an incline is detected (e.g., using an altimeter, a barometer, a GPS system, accelerometer data, or a heart rate to cadence correlation), an adjustment factor may be applied to the stride length correlation data 240. For example, when a user is detected to be walking uphill, the stride length associated with specific gait characteristics may be shortened. Where an uphill or downhill locomotion is detected, distance logic 215 may also monitor a vertical distance traveled.

In one embodiment, motion processor 120 includes attribute logic 225. Attribute logic 225 may detect one or more attributes of a user. In one embodiment, detecting an attribute of a user includes receiving user input of the user attribute 250. For example, a user may be prompted to input a user weight, height, gender, age, fitness, etc. In one embodiment, this data may be obtained from other sources. For example, a user may provide access to medical records or other sources of such data. Alternatively, attribute logic 225 may analyze acceleration measurement data 175 and/or user activity statistics 235 to determine one or more attributes of the user. The analysis and/or determination of user attributes 250 may be performed automatically on a periodic or continuous basis. Alternatively, the analysis and/or determination may be performed upon receiving a calibration command (e.g., from a user, or from a trigger).

In one embodiment, user height and weight are determined by attribute logic 225. On average, users having a specific height and weight exhibit a certain set of gait characteristics. For example, in general, at a given speed the taller an individual, the slower their step cadence and the longer their stride. Moreover, the step cadence of heavier individuals may also be faster than that of lighter individuals at a given speed.

Such gait characteristics may be determined from stored acceleration measurement data. Alternatively, a gait characteristic log (not shown) may be maintained in memory 115.

In one embodiment, user athletic ability is determined by attribute logic 225. User athletic ability may be determined by analyzing user activity statistics 235 and/or acceleration measurement data 175. For example, user athletic ability may be determined by calculating the amount of exercise that has been recorded for the user over the last week, month, etc. Attribute logic 225 may examine a number of steps per workout, an average distance per workout, number of workouts over a time period, duration of each workout, etc. In one embodiment, the intensity of the exercise, and when available the heart rate data associated with the exercise, may also be used to determine athletic ability. Based on these user activity statistics 235, for example, a numeric value may be generated that reflects the general fitness level of the user. For example, a fitness level of 1 may indicate that a user does not exercise frequently, and is generally unfit. A fitness level of 5, on the other hand, may indicate that a user exercises frequently, and is generally fit, while a fitness level of 10 may indicate that the user is a professional athlete.

Attribute logic 225 may modify stored user attributes 250 based on detected user attributes. Such modification may occur when stored user attribute 250 entries differ from detected user attributes. In one embodiment, a user attribute is modified if the stored user attribute 250 differs from a detected user attribute by at least a threshold amount. For example, if faulty attribute data is stored (e.g., user entered a weight of 500 lbs. and 5' when he was 200 lbs. and 6'), attribute logic 225 may detect that the gait characteristics do not match such user attributes. Attribute logic 225 may then adjust such detected faulty attributes. Attribute logic 225 may also make adjustments to stored user attributes 250 as a user gains or loses weight, improves his or her athletic ability, etc. In one embodiment, if such a discrepancy is detected, attribute logic 225 may generate a notification for the user, and prompt the user to correct the data.

When a user first uses electronic device 100, stride length correlation data 240 may not be calibrated to that user. Initially, stride length correlation data 240 may include a default data structure and/or algorithm that relates gait characteristics to stride lengths. In one embodiment, the default data structure and/or algorithm represent gait characteristic vs. stride length for an average person (e.g., 5'10", 180 lbs., 30 years old, average athletic fitness, etc.). The further a user differs from the assumed average person, the greater a deviance between a distance measured and a distance actually traveled.

Calibration logic 220 may calibrate (e.g., update or replace) stride length correlation data 240 to improve its accuracy based on actual data received. In one embodiment, calibration logic 220 calibrates the stride length correlation data 240 based on the user attributes received and/or determined by attribute logic 225. In general, a step having a specific gait characteristic or gait characteristics will have a specific stride length for a given user. Factors that may affect the relationship between the stride length and the gait characteristics include user weight, height, age, gender, athletic ability, etc. Therefore, when one or more of these user attributes 250 is known, a more accurate stride length can be determined for each step. In turn, a more accurate total distance traveled and speed of travel can be determined.

In another embodiment, calibration logic 220 calibrates stride length correlation data 240 based on received empirical distance information. Such received distance information may be correlated to gait characteristics that were collected while the received distance was walked or run. This correlation may then be compared to the stride length correlation data 240. If the correlation based on the received distance information does not match the stride length correlation data 240, then the stride length correlation data may be modified or replaced.

Received distance information may be collected from a GPS unit, gathered using network triangulation (e.g., of cell phone towers), gathered based on a known distance between RFID readers, input by a user, etc. Calibration logic 220 may then automatically calibrate the stride length correlation data 240 based on the received distance information. In one embodiment, this calibration requires that the user maintain a steady cadence during the entire distance being analyzed.

In one embodiment, calibrating the stride length correlation data 240 includes generating a new data structure using a data structure generation algorithm. The data structure generation algorithm may use as inputs the user attributes and/or a stride length vs. gait characteristic correlation determined based on received distance information. Therefore, a new data structure can be produced that is tailored to the user attributes of a specific user and/or based on empirical data taken of the specific user. Each entry in the new data structure may be more accurate for the user than entries in an uncalibrated data structure.

In another embodiment, calibrating the stride length correlation data 240 includes adjusting entries in an existing data structure. Such adjustments may include shifting entries (e.g., adjusting entry values up or down), compressing entries (e.g., causing entries to represent a smaller range of gait characteristics), stretching entries (e.g., causing entries to represent a greater range of gait characteristics), scaling entries (e.g., multiplying entries by a percentage or scaling factor), etc. Adjustments may be made based on one or more of user attributes and a stride length vs. gait characteristic correlation determined based on received distance information. For example, a global shift may be applied to entries if a user walked 1 mile, but a distance of 1.5 miles was measured. Such a global shift could include shifting down the entries to reflect that the actual stride length is shorter than represented by the data structure. Alternatively, if only a few entries in the data structure are off, then only those entries may be shifted.

In yet another embodiment, calibrating the stride length correlation data 240 includes modifying a stride length algorithm. Constants and/or variables that apply to user attributes may be modified. Moreover, adjustments may be made to the algorithm based on a stride length vs. gait characteristic correlation determined based on received distance information.

In one embodiment, a new data structure is generated when the stride length correlation data is first calibrated (e.g., when user attributes are first detected), and the new data structure is adjusted for subsequent calibrations.

In addition to calibrating stride length correlation data 240, calibration logic 220 may also calibrate incline correlation data (not shown). Incline correlation data may correlate inclines to combinations of heart rates and cadences. Therefore, for example, if a specific incline and a specific heart rate are detected, then an incline may be estimated. In one embodiment, an incline is estimated by comparing a change in heart rate vs. cadence over time. Therefore, for example, if a heart rate to cadence ratio increases by a specific amount, then it may be determined that an incline on which a user is walking or running has changed by an amount corresponding to the ratio increase. The more acceleration measurement data and/or heart rate data available to calibration logic, the more exact a calibration of the incline correlation data may be.

Calibration logic 220 may further calibrate an incline adjustment factor (not shown). The incline adjustment factor may be applied to the stride length correlation data when an incline is detected. For example, when a user walks uphill, the user is likely to take smaller steps than when that user walks on level terrain. This difference in stride length may be accounted for using the incline adjustment factor. A value of the incline adjustment factor that is applied to the stride length correlation data 240 may depend on a degree of incline and on user attributes. The incline adjustment factor may be calibrated in the manners discussed above with reference to the stride length correlation data 240. The incline adjustment factor may also be used in the competition logic 155, discussed above with respect to FIG. 1, to normalize distance.

Figure 3:
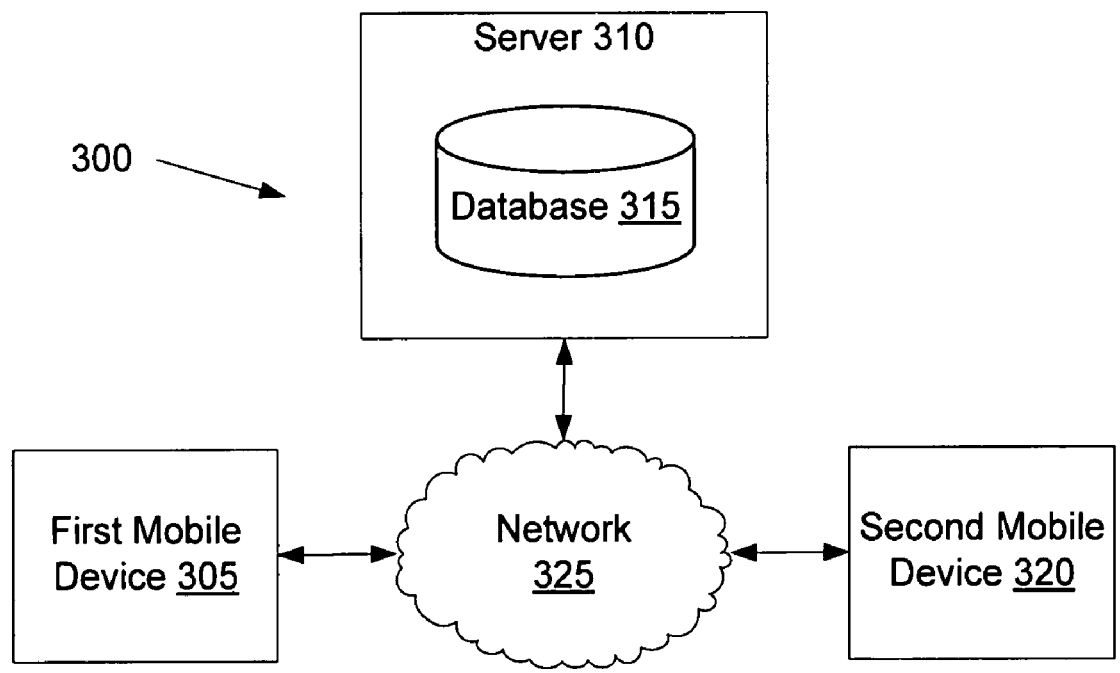
FIG. 3 illustrates a block diagram of an activity monitoring system, in accordance with one embodiment of the present invention.

FIG. 3 illustrates a block diagram of an activity monitoring system 300, in accordance with one embodiment of the present invention. The activity monitoring system 300 may monitor the activity of one or more users connected thereto. Records of such user activity may be maintained by the activity monitoring system 300, and may be compared to user activity of other users. In one embodiment, the activity monitoring system 300 includes a first mobile device 305, server 310 and second mobile device 320. In another embodiment, the activity monitoring system 300 may not include a server 310. In still other embodiments, activity monitoring system 300 may include greater or fewer mobile devices than shown, and may include more than one server.

In the illustrated embodiment, first mobile device 305, second mobile device 320 and server 310 are connected via network 325, which may be a public network (e.g., internet) or private network (e.g., local area network (LAN), intranet, etc.). Alternatively, connections may be established directly between devices (e.g., directly between mobile devices, or directly between server 310 and a mobile device). Wireless connections may be established (directly between devices or via network 325) using any wireless data transfer protocol, such as Bluetooth, radiofrequency (RF), wireless local area network (WLAN), infrared, cellular networks including global system for mobile communications (GSM), code division multiple access (CDMA), integrated digital enhanced network (iDEN), etc. Wired connections may be established using firewire, Ethernet, universal serial bus (USB), etc.

The first mobile device 305 and second mobile device 320 may be any electronic devices capable of establishing connections (wireless or wired) to other devices. In one embodiment, the first mobile device 305 and second mobile device 320 correspond to electronic device 100 of FIG. 1.

Referring to FIG. 3, server 310 may be a personal computer (desktop or laptop), network server, game kiosk, etc. Server 310 may receive user activity statistics, gait characteristics, acceleration measurement data, etc. from the first mobile device 305, second mobile device 320 and/or additional mobile devices (not shown). Such data may be stored in a database 315. The database 315 may include a broad user base of stride length correlation data, gait characteristics, user activity statistics, and so on.

Through statistical analysis, stride length vs. gait characteristic data may be determined and/or refined. As additional data is added to the database 315, algorithms used to generate stride length correlation data for mobile devices may improve. Such improved algorithms may periodically be downloaded to the mobile devices to update them. Alternatively, data stored in the database 315 relevant to, for example, a user of the first mobile device 305 (e.g., data collected from other users with the same user attributes) may be used to update an algorithm or data structure (e.g., a lookup table) specific to the user of the first mobile device 305. To update the algorithm or data structure, the relevant data may be downloaded to the first mobile device 305. In one embodiment, first mobile device 305 is updated automatically when a new update is available. Alternatively, an update may be initiated upon a user update command.

First mobile device 305 and second mobile device 320 may be participants in a competition, as described above with reference to competition logic 155 of FIG. 1. The competition may be, for example, a running competition, a walking competition, etc., and may be a live competition or a time-shifted competition. If the competition is a live competition, race data may be streamed between the first mobile device 305 and second mobile device 320 during the competition. If the competition is a time-shifted competition, once a first user (e.g. of first mobile device 305) completes his or her portion of the competition, race data based on the completed portion of the competition may be uploaded to server 310 and/or to second mobile device 320. A second user of second mobile device 320 may then be able to compare his/her performance data with the downloaded race data as he/she completes his/her portion of the competition.

Figure 4:
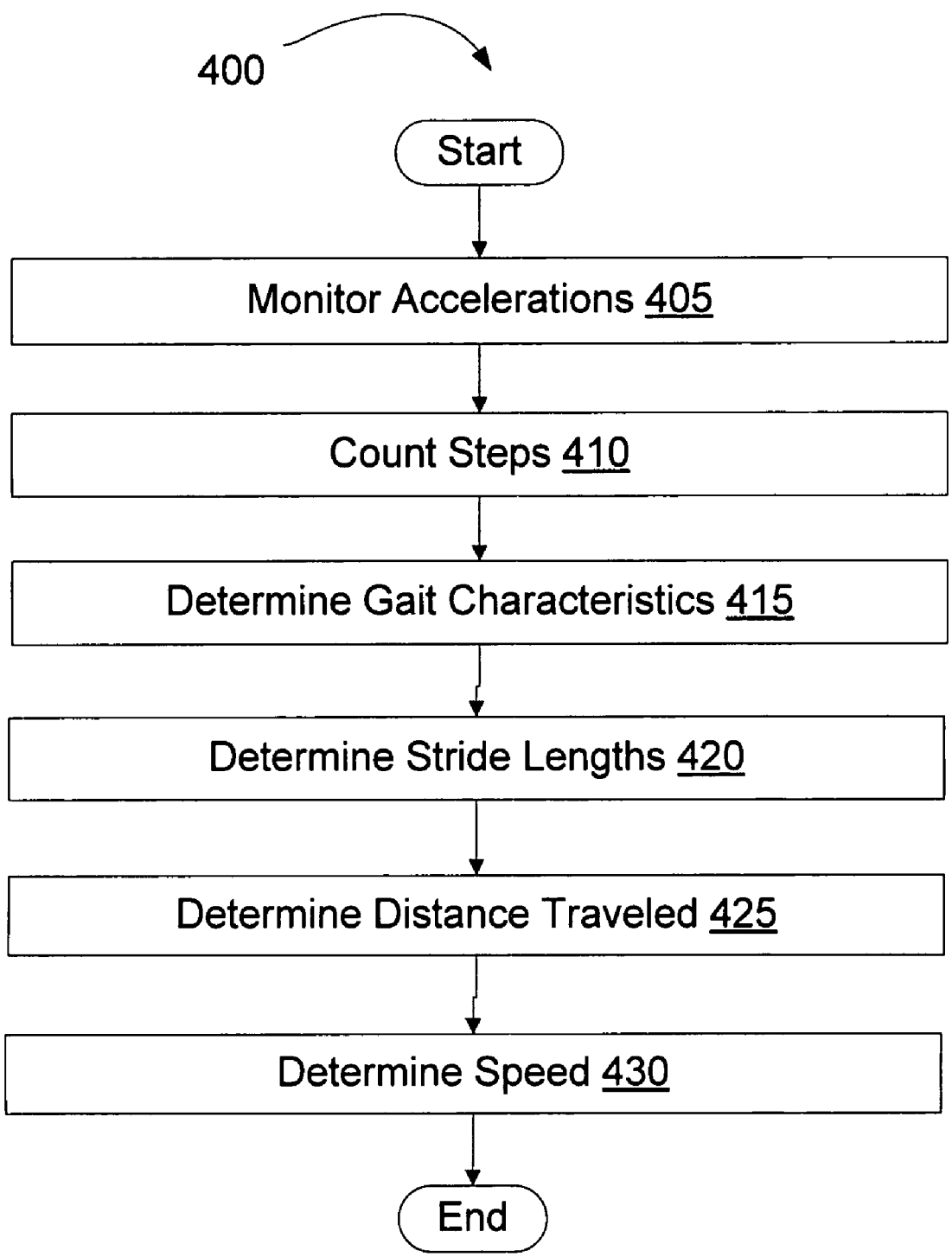
FIG. 4 illustrates a flow diagram for a method of monitoring human activity using an inertial sensor, in accordance with one embodiment of the present invention.

FIG. 4 illustrates a flow diagram for a method 400 of monitoring human activity using an inertial sensor, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 400 is performed by the electronic device 100 of FIG. 1.

Referring to FIG. 4, method 400 begins with monitoring accelerations (block 405). Monitoring accelerations may include obtaining acceleration measurement data from one or more inertial sensors and/or other acceleration monitoring devices. At block 410, the accelerations are processed to count a number of steps. Steps may be counted when one or more motion criteria are satisfied by the acceleration measurement data.

At block 415, gait characteristics associated with the counted steps are determined. Determining gait characteristics may include examining the acceleration measurement data to determine one or more of a cadence, heel strike, foot liftoff, etc.

At block 420, stride lengths are determined for the steps based on the determined gait characteristics. In one embodiment, the gait characteristics are used as inputs into a stride length algorithm, an output of which is a stride length. In another embodiment, an entry in a data structure (e.g., a lookup table) associating the determined gait characteristics with a specific stride length is located. The associated stride length may be the stride length of the steps.

At block 425, a distance traveled is determined. The distance traveled may be determined by adding up the stride lengths of the counted steps. At block 430, a speed of travel is determined. The speed of travel may include an average speed of travel, a current speed of travel, etc. Speed of travel may be determined by dividing a distance traveled by an amount of time. The process, in one embodiment, continues to monitor the user's step cadence and other functions, to maintain a total distance traveled. In one embodiment, the user may access distance traveled and speed of travel. In one embodiment, a total distance traveled is maintained on a daily, weekly, or other appropriate basis. In one embodiment, an average speed is also maintained on a daily, weekly, or other appropriate basis.

Figure 5:
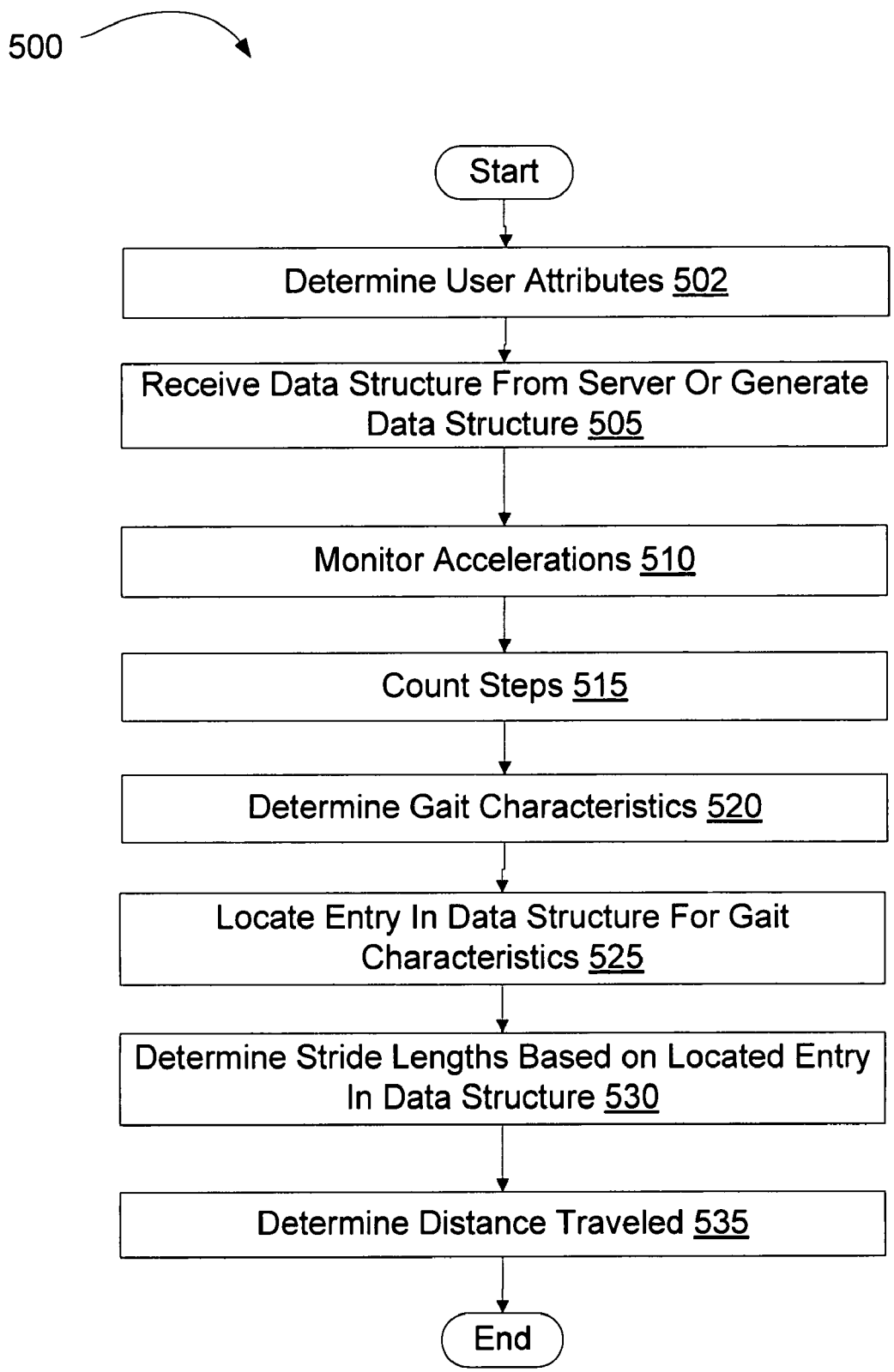
FIG. 5 illustrates a flow diagram for a method of monitoring human activity using an inertial sensor, in accordance with another embodiment of the present invention.

FIG. 5 illustrates a flow diagram for a method 500 of monitoring human activity using an inertial sensor, in accordance with another embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 500 is performed by the electronic device 100 of FIG. 1.

Referring to FIG. 5, method 500 begins with determining one or more user attributes (block 502). User attributes may include weight, height, gender, age, athletic ability, etc. In one embodiment, one or more user attributes are input by a user. In another embodiment, one or more user attributes are automatically detected (e.g., by an attribute logic 225 of FIG. 2). The user attributes may be detected based on stored acceleration measurement data and/or user activity statistics. In one embodiment, attributes are obtained from another data source, and downloaded.

At block 505, a data structure is obtained. The data structure may be a lookup table that includes multiple entries. Each entry may associate one or more gait characteristics with a specific stride length. In one embodiment, the data structure is received from a server or other computing device. Alternatively, the data structure may be generated. In one embodiment, the data structure is generated by a data structure algorithm that generates a data structure specific to the determined user attributes.

At block 510, accelerations are monitored. At block 515, the accelerations are processed to count a number of steps. At block 520, gait characteristics associated with the counted steps are determined. At block 525, an entry in the data structure is located for the determined gait characteristics. At block 530, the stride lengths are determined based on the located entry in the data structure. At block 535, a distance traveled is determined. The method continues to monitor accelerations, count steps, and calculate the distance traveled until the user stops moving. In one embodiment, a cumulative distance is maintained on a daily basis.

Figure 6:
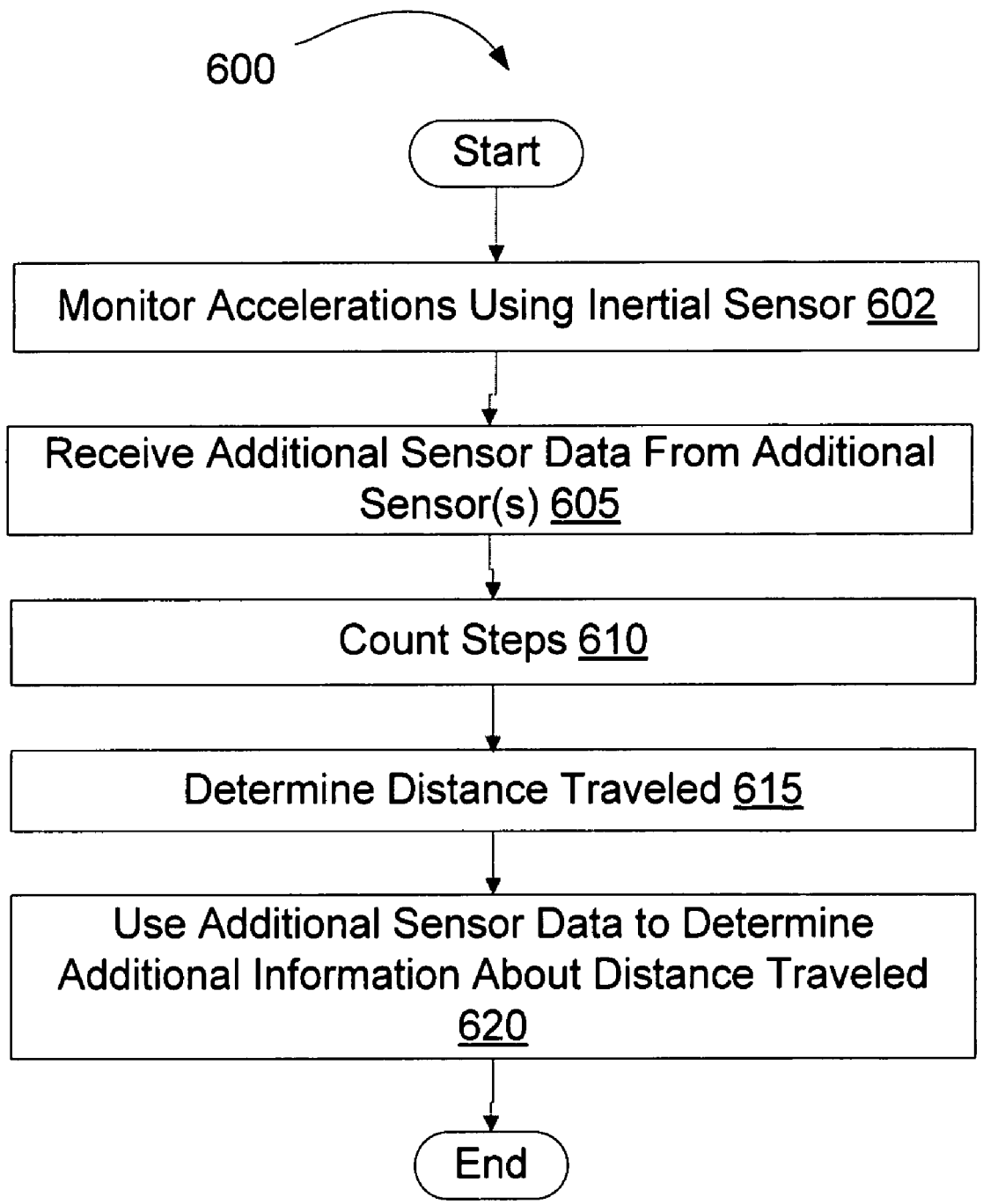
FIG. 6 illustrates a flow diagram for a method of monitoring human activity using an inertial sensor, in accordance with yet another embodiment of the present invention.

FIG. 6 illustrates a flow diagram for a method 600 of monitoring human activity using an inertial sensor, in accordance with yet another embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 600 is performed by the electronic device 100 of FIG. 1.

Referring to FIG. 6, method 600 begins with monitoring accelerations (block 602). Monitoring accelerations may include obtaining acceleration measurement data from one or more inertial sensors and/or other acceleration monitoring devices.

At block 605, additional sensor data is received form additional sensors. In one embodiment, heart rate data is received from a heart rate sensor (e.g., EKG). Alternatively, other sensor data (e.g., pressure, temperature, direction, etc.) may be received from other sensors (e.g., altimeter, thermometer, thermistor, magnetometer, etc.)

At block 610, the accelerations are processed to count a number of steps. Steps may be counted when one or more motion criteria are satisfied by the acceleration measurement data.

At block 615, a distance traveled is determined. Determining the distance traveled may include determining gait characteristics associated with the counted steps. Then, the system may calculate a stride length, and based on a number of steps and the stride length, a distance traveled is calculated.

At block 620, the additional sensor data is used to determine additional information about the distance traveled. For example, if a user cadence has remained steady or decreased, but a heart rate has increased, it may be determined that the distance traveled was at an incline. Alternatively, an incline and/or altitude may be determined and associated with the distance based on a pressure sensor. Other information may also be deduced using different combinations of sensors.

Additional sensor data may also be used to adjust the distance traveled. In one embodiment, the additional sensor data is used to determine an incline. The incline may then be used to adjust the stride length associated with steps taken at the determined incline. This adjustment is then made to the distance traveled. The process continues until the user's cadence changes or the user stops moving. The process then ends.

Figure 7A:
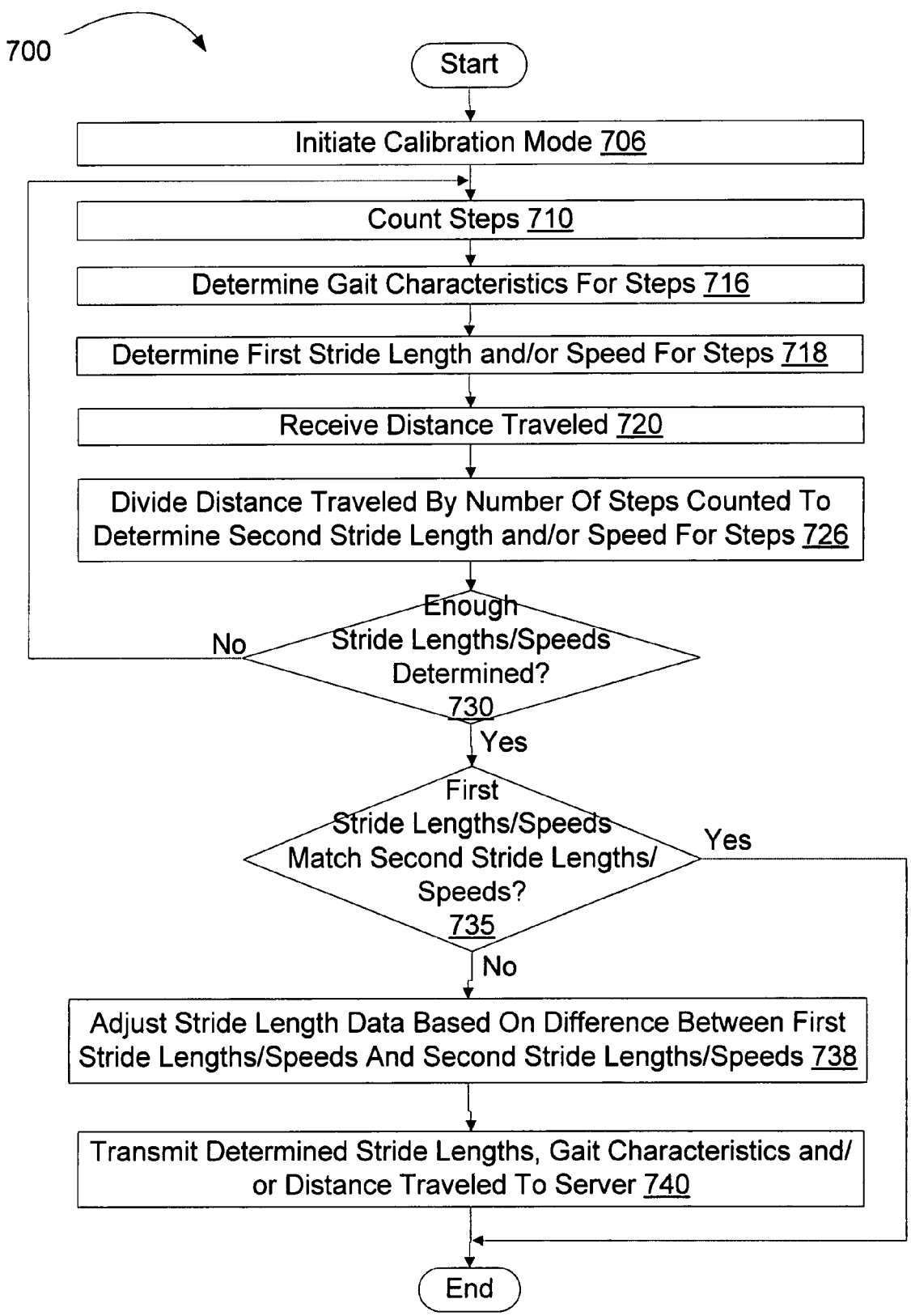
FIG. 7A illustrates a flow diagram for a method of calibrating an electronic device, in accordance with one embodiment of the present invention.

FIG. 7A illustrates a flow diagram for a method 700 of calibrating an electronic device, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 700 is performed by the electronic device 100 of FIG. 1.

Referring to FIG. 7A, method 700 begins with initiating a calibration mode (block 706). The calibration mode may be initiated by a user, or automatically based on one or more calibration triggers. For example, calibration may be automatically initiated periodically (e.g., every day, week, or month, every 10,000 steps counted, etc.). In another example, calibration may be initiated automatically when an external calibration data provider is detected (e.g., an RFID reader is detected, a GPS signal is detected, a cellular signal is detected, etc.).

At block 710, steps are counted. Steps may be counted based on acceleration measurement data collected by an inertial sensor. At block 716, gait characteristics for the steps are determined. At block 718 a first stride length is determined for the steps. Alternatively, or in addition, a first speed may be determined for the steps. The first speed may be determined by comparing the stride lengths to a time in motion. In one embodiment, the first speed is an average speed averaging speeds associated with each of the steps measured while a user was in motion.

At block 720, distance information is received for the actual distance traveled. The distance information may be input by a user. Alternatively, the distance information may be automatically received based on one or more of a GPS signal, network triangulation, etc.

At block 726, the received distance traveled is divided by the number of steps counted to determine a second stride length for the steps. Alternatively, or in addition, a second speed may be determined by dividing the received distance traveled by the time in motion.

At block 730, it is decided whether enough stride lengths and/or speeds have been determined. In one embodiment, at least two different stride lengths and/or speeds should be determined to calibrate stride length correlation data. Therefore, a user may walk a fixed distance at least twice, each time using a different stride length and/or speed. This may provide sufficient stride length correlation data to extrapolate and/or interpolate additional stride lengths. In one embodiment, only a single stride length and/or speed needs to be determined. If not enough stride lengths and/or speeds have been determined, the method returns to block 710 and continues to count steps. If enough stride lengths and/or speeds have been determined, the method proceeds to block 735.

At block 735, first stride lengths (based on stride length correlation data) may be compared to second stride lengths (based on received distance information). Alternatively, or in addition, the first speeds may be compared to the second speeds. If the first stride lengths match the second stride lengths and/or the first speeds match the second speeds, no adjustment is necessary and the method ends. If the first stride lengths do not match the second stride lengths and/or the first speeds do not match the second speeds, the method proceeds to block 738.

At block 738, stride length correlation data is updated (adjusted) based on a difference between the first stride lengths (stride lengths based on stride length correlation data) and the second stride lengths (stride lengths based on received distance information). Alternatively, or in addition, the stride length correlation data may be updated based on a difference between the first speeds and the second speeds. In one embodiment, stride length correlation data is updated only for the gait characteristics associated with the first stride lengths and/or speeds used by the system in the initial calculation. In another embodiment, the stride length correlation data for other gait characteristics may also be updated based on interpolated and/or extrapolated stride lengths and/or speeds. For example, if all first stride lengths measured 0.1 ft. less than all second stride lengths, then all stride lengths (e.g., all entries within a stride length data structure) may be increased by 0.1 ft. Moreover, if all first speeds measured 0.5 mph faster than the second speeds, then all stride lengths may be adjusted such that the first speeds would be reduced by 0.5 mph. In one embodiment, updating the stride length correlation data includes updating entries in a data structure. Alternatively, updating the stride length correlation data may include updating a stride length algorithm that takes as an input one or more gait characteristics, and produces as an output a stride length.

At block 740, in one embodiment, the determined stride lengths, gait characteristics and/or distance traveled are transmitted to a server. In one embodiment, if no adjustment of the data structure is needed, only a confirmation message is sent to the server. The server may add this adjustment information to a database of stride length vs. gait characteristic data.

Figure 7B:
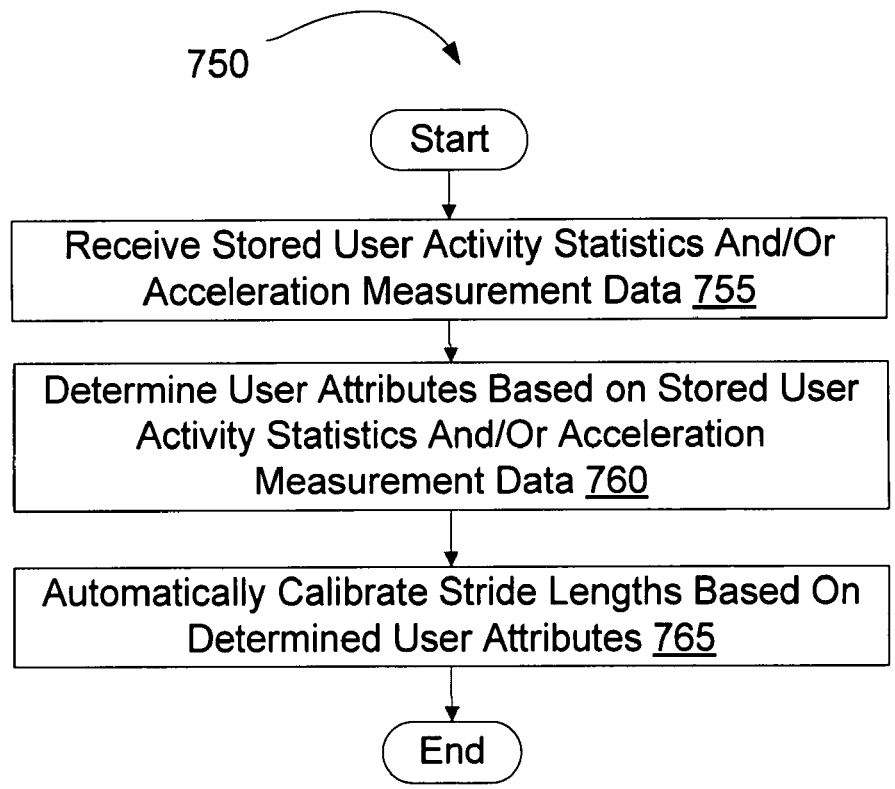
FIG. 7B illustrates a flow diagram for a method of calibrating an electronic device, in accordance with another embodiment of the present invention.

FIG. 7B illustrates a flow diagram for a method 750 of calibrating an electronic device, in accordance with another embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 750 is performed by the electronic device 100 of FIG. 1.

Referring to FIG. 7B, method 750 begins with receiving stored user activity statistics and/or acceleration measurement data (block 755). User activity statistics may include a number of steps (total, per day, per week, etc.), distance traveled, frequency of exercise, etc.

At block 760, one or more user attributes are determined based on the stored user activity statistics and/or acceleration measurement data. In one embodiment, an approximate user height, user weight, user gender, etc. are determined. In another embodiment, a user athletic ability level is determined.

At block 765, stride lengths are automatically calibrated based on the determined user attributes, and cadences. Stride lengths may be adjusted as discussed above with reference to calibration logic 220 of FIG. 2. The method then ends.

Figure 7C:
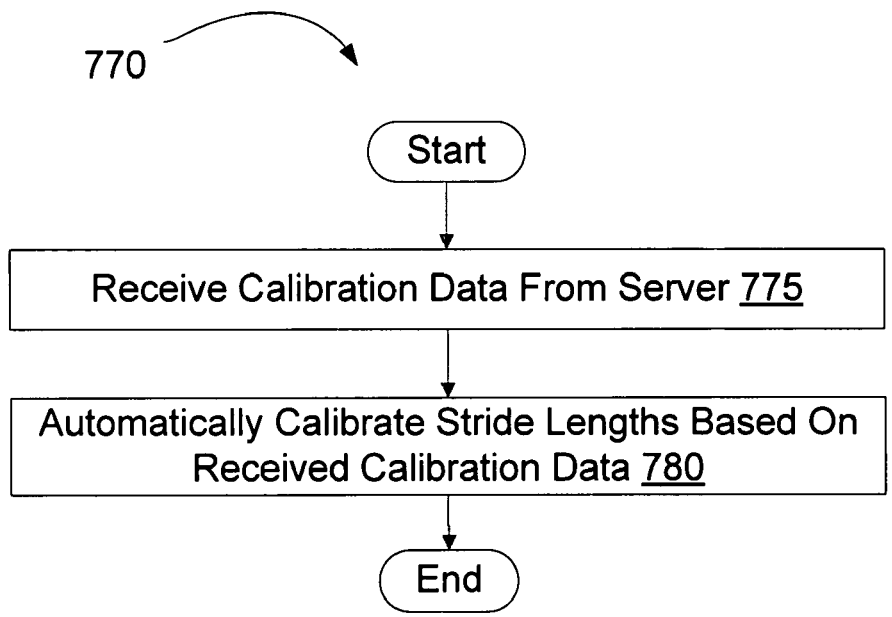
FIG. 7C illustrates a flow diagram for a method of calibrating an electronic device, in accordance with yet another embodiment of the present invention.

FIG. 7C illustrates a flow diagram for a method 770 of calibrating an electronic device, in accordance with yet another embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 770 is performed by the electronic device 100 of FIG. 1.

Referring to FIG. 7C, method 770 begins with receiving calibration data from a server (block 775). Calibration data may include one or more of an algorithm for generating a stride length correlation data structure, an algorithm for determining stride lengths, and a data structure with multiple entries, each of which associates one or more gait characteristics with a stride length. Alternatively, calibration data may include one or more correction factors to apply to an algorithm or data structure used to determine stride lengths associated with gait characteristics.

At block 780, stride lengths are automatically calibrated based on the received calibration data. Calibrating the stride lengths may include replacing an existing algorithm and/or data structure. Alternatively, calibrating the stride lengths may include updating (e.g., applying correction factors to) an existing algorithm and/or data structure.

Figure 8:
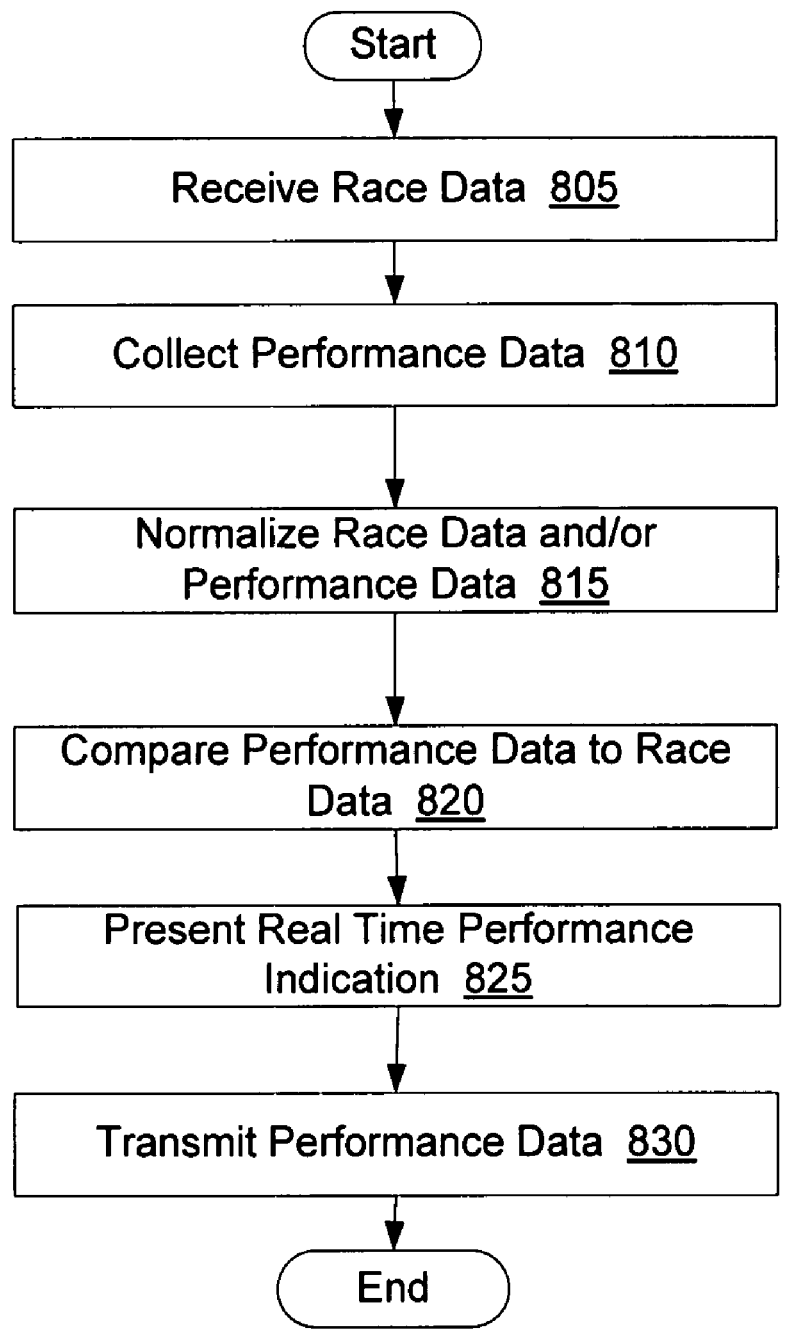
FIG. 8 illustrates a flow diagram for a method of comparing performance data, in accordance with one embodiment of the present invention.

FIG. 8 illustrates a flow diagram for a method 800 of comparing performance data, in accordance with one embodiment of the present invention. In one embodiment, the performance data is compared to determine competitor placements in a race. The method may be performed by processing logic that may comprise hardware (e.g., circuitry, dedicated logic, programmable logic, microcode, etc.), software (such as instructions run on a processing device), or a combination thereof. In one embodiment, method 800 is performed by the electronic device 100 of FIG. 1.

Referring to FIG. 8, method 800 begins with receiving race data (block 805). Race data may include distance and/or speed data collected by one or more electronic devices of one or more users. Race data may be received from a server or another mobile device.

At block 810, performance data is collected. Performance data may include distance and/or speed data collected by an electronic device currently being used.

At block 815, one or more of the race data and the performance data is normalized. Normalizing the data may include applying a modifier or offset to the data. Race data and performance data may be normalized for incline, altitude, temperature, etc. This ensures that a competition remains fair even though different competitors may compete in different locations with different terrain characteristics, and at different times. In one embodiment, normalization may further include adjustment for relative athletic ability, height, age, and other user characteristics.

At block 820, the performance data of the current user is compared to the race data. At block 825, a real time performance indication is presented. The real time performance indication may be presented in a display, or via one or more feedback elements. For example, aural or tactile feedback may be used to notify a user that he/she is falling behind, that he/she is gaining on another competitor, etc.

At block 830, the performance data is transmitted. This may occur after the user has finished the competition (e.g., finished the race). Alternatively, performance data may be streamed as it is collected, or transmitted periodically. The performance data may be transmitted to mobile computing devices and/or a server. In one embodiment, the performance data is made available to other competitors to enable those competitors to compete against it in a real time or time-shifted race. The method then ends.

Figure 9:
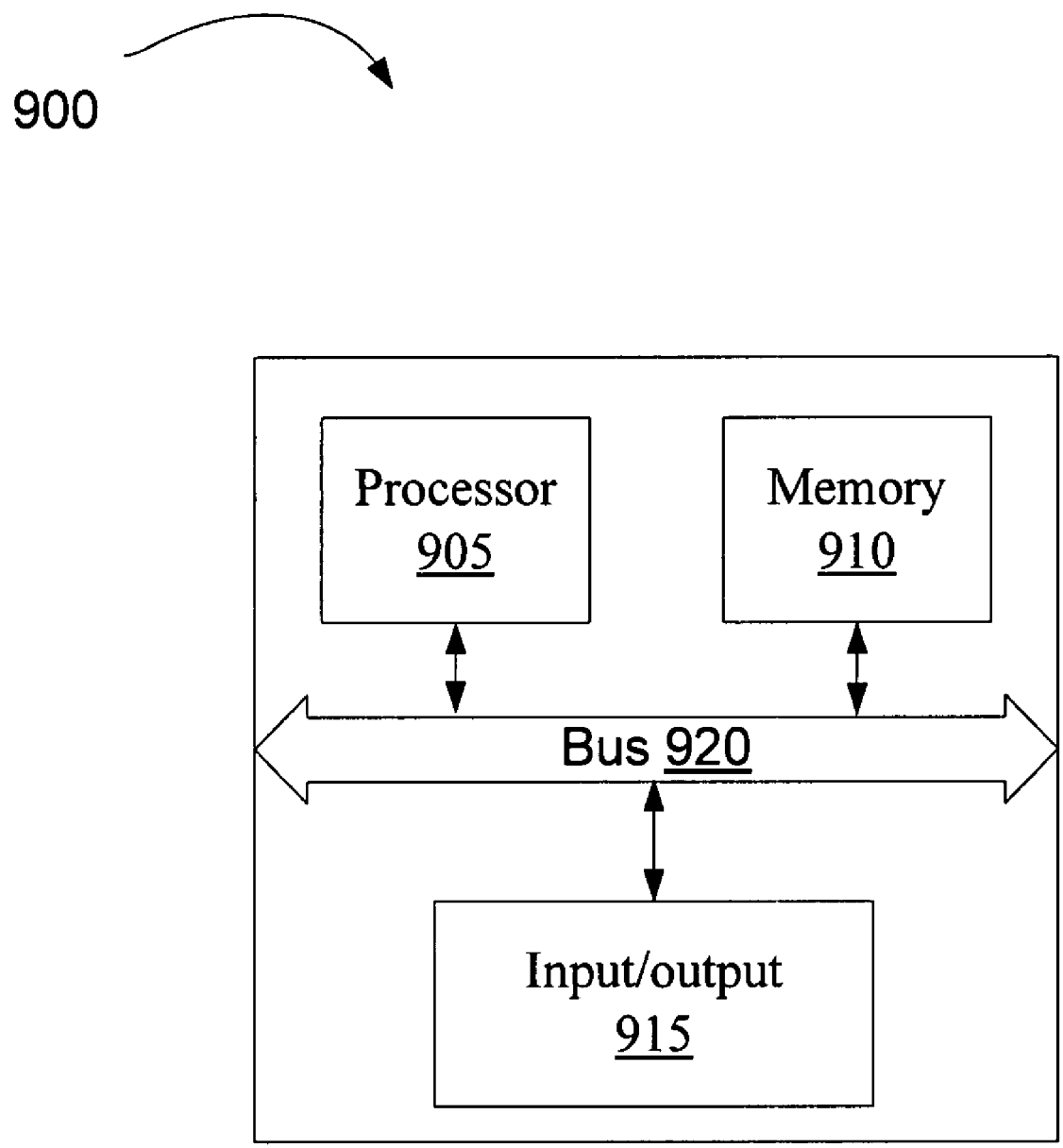
FIG. 9 illustrates a block diagram of a machine in the exemplary form of a computer system, in accordance with one embodiment of the present invention.

FIG. 9 illustrates a block diagram of a machine in the exemplary form of a computer system 900 within which a set of instructions, for causing the machine to perform any one or more of the methodologies discussed herein, may be executed. The exemplary computer system 900 includes a processing device (processor) 905, a memory 910 (e.g., read-only memory (ROM), a storage device, a static memory, etc.), and an input/output 915, which communicate with each other via a bus 920. Embodiments of the present invention may be performed by the computer system 900, and/or by additional hardware components (not shown), or may be embodied in machine-executable instructions, which may be used to cause processor 905, when programmed with the instructions, to perform the method described above. Alternatively, the method may be performed by a combination of hardware and software.

Processor 905 represents one or more general-purpose processing devices such as a microprocessor, central processing unit, or the like. More particularly, the processor 905 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 905 may also be one or more special-purpose processing devices such as an application specific integrated circuit (ASIC), a field programmable gate array (FPGA), a digital signal processor (DSP), network processor, or the like.

The present invention may be provided as a computer program product, or software, that may be stored in memory 910. Memory 910 may include a machine-readable medium having stored thereon instructions, which may be used to program exemplary computer system 900 (or other electronic devices) to perform a process according to the present invention. Other machine-readable mediums which may have instruction stored thereon to program exemplary computer system 900 (or other electronic devices) include, but are not limited to, floppy diskettes, optical disks, CD-ROMs, and magneto-optical disks, ROMs, RAMs, EPROMs, EEPROMs, magnetic or optical cards, flash memory, or other type of media or machine-readable mediums suitable for storing electronic instructions.

Input/output 915 may provide communication with additional devices and/or components. In one embodiment, input/output 915 may transmit data to and receive data from, for example, networked computers, servers, mobile devices, etc.

In the foregoing description, numerous specific details have been set forth such as examples of specific systems, languages, components, etc. in order to provide a thorough understanding of the present invention. It will be apparent, however, to one skilled in the art that these specific details need not be employed to practice the present invention. In other instances, well known materials or methods have not been described in detail in order to avoid unnecessarily obscuring the present invention.

In the foregoing specification, the invention has been described with reference to specific exemplary embodiments thereof. It will, however, be evident that various modifications and changes may be made thereto without departing from the broader scope of the invention as set forth in the appended claims. The specification and drawings are, accordingly, to be regarded in an illustrative rather than a restrictive sense.

What is claimed is:

1. A method of monitoring human activity by a mobile device, comprising:
    monitoring accelerations using an inertial sensor disposed at one of a plurality of locations on a human body, wherein at least one of the plurality of locations is not a foot location;
    counting a plurality of steps based on the accelerations;
    determining a gait characteristic of the plurality of steps;
    determining one or more user attributes based at least in part on historical data collected by the inertial sensor;
    using a stride length to gait characteristic correlation to determine a stride length from the gait characteristic, wherein the correlation is based at least in part on the determined one or more user attributes; and
    determining at least one of a distance traveled and a speed of travel based on the stride length.

2. The method of claim 1, wherein the gait characteristic comprises a step cadence.

3. The method of claim 1, wherein determining the stride length includes locating a stride length associated with the gait characteristic in a data structure.

4. The method of claim 3, wherein the data structure includes a plurality of entries, each of the plurality of entries associating a distinct stride length with one or more distinct gait characteristics, further comprising:
    modifying the data structure based on the one or more user attributes to calibrate the stride length by changing one or more of the plurality of entries.

5. The method of claim 3, further comprising:
    receiving a user input of one or more user attributes; and
    generating the data structure using the one or more user attributes.

6. The method of claim 1, further comprising:
    receiving distance information; and
    automatically calibrating the stride length based on the received distance information.

7. The method of claim 6, wherein the distance information is based on at least one of global positioning system (GPS) data, network triangulation data, or user input, the method further comprising:
    adjusting the stride length based on a difference between the received distance information and the determined distance traveled.

8. The method of claim 1, further comprising:
    receiving a heart rate from a heart rate sensor; and
    determining information about the distance traveled based on the heart rate.

9. The method of claim 8, wherein determining information comprises determining an incline, and adjusting the stride length to gait characteristic correlation based on the incline using an incline adjustment factor.

10. The method of claim 1, further comprising:
    comparing the distance traveled and the speed of travel to stored race data to generate a comparison result; and
    presenting a real time performance indication that includes the comparison result.

11. The method of claim 10, further comprising:
    receiving the stored race data from one of a server and a mobile device.

12. The method of claim 10, further comprising:
    normalizing at least one of the distance traveled, the speed of travel, the stored distance traveled, and the stored speed of travel before comparing.

13. A mobile apparatus comprising:
    an inertial sensor to monitor accelerations from one of a plurality of locations on a body, wherein at least one of the plurality of locations is not a foot location;
    a step counting logic coupled with the inertial sensor to count a plurality of steps based on the accelerations;

a gait logic coupled with the step counting logic to determine a gait characteristic of the plurality of steps;
an attribute logic to determine one or more user attributes based at least in part on historical data collected by the inertial sensor; and
a distance logic coupled with the gait logic to determine a stride length of the plurality of steps based on the gait characteristic and the one or more user attributes, and to apply the stride length to the plurality of steps to determine at least one of a distance traveled and a speed of travel.

14. The mobile apparatus of claim 13, further comprising:
a calibration logic connected with the distance logic, the calibration logic to receive distance information and to automatically calibrate the stride lengths based on the received distance information.

15. The mobile apparatus of claim 13, further comprising:
the attribute logic to calibrate the stride length according to the one or more user attributes.

16. The mobile apparatus of claim 13, further comprising:
the distance logic to determine information about the distance traveled based on a heart rate of the user.

17. The mobile apparatus of claim 16, wherein determining information comprises determining an incline, the apparatus further comprising:
the distance logic to adjust a stride length to gait characteristic correlation based on the incline using an incline adjustment factor.

18. The mobile apparatus of claim 13, further comprising:
a competition logic to compare the distance traveled and the speed of travel to stored race data to generate a comparison result, and to present a real time performance indication that includes the comparison result.

19. The mobile apparatus of claim 13, further comprising:
a competition logic to enable users to set up time shifted races.

20. A machine-accessible storage medium including instructions that, when executed by a machine, cause the machine to perform a method comprising:
monitoring accelerations using an inertial sensor disposed at one of a plurality of locations on a human body, wherein at least one of the plurality of locations is not a foot location;
counting a plurality of steps based on the accelerations;
determining a gait characteristic of the plurality of steps;
determining one or more user attributes based at least in part on historical data collected by the inertial sensor;
using a stride length to gait characteristic correlation to determine a stride length from the gait characteristic, wherein the correlation is based at least in part on the determined one or more user attributes; and
determining at least one of a distance traveled and a speed of travel based on the stride length.

21. The machine-accessible storage medium of claim 20, wherein the gait characteristic comprises a step cadence.

22. The machine-accessible storage medium of claim 20, wherein determining the stride length includes locating a stride length associated with the gait characteristic in a data structure.

23. The machine-accessible storage medium of claim 22, wherein the data structure includes a plurality of entries, each of the plurality of entries associating a distinct stride length with one or more distinct gait characteristics, further comprising:
modifying the data structure based on the one or more user attributes to calibrate the stride length by changing one or more of the plurality of entries.

24. The machine-accessible storage medium of claim 22, the method further comprising:
receiving a user input of one or more user attributes; and
generating the data structure using the one or more user attributes.

25. The machine-accessible storage medium of claim 20, the method further comprising:
receiving distance information; and
automatically calibrating the stride length based on the received distance information.

26. The machine-accessible storage medium of claim 25, wherein the distance information is based on at least one of: global positioning system (GPS) data, network triangulation data, or user input, the method further comprising:
adjusting the stride length based on a difference between the received distance information and the determined distance traveled.

27. The machine-accessible storage medium of claim 20, the method further comprising:
receiving a heart rate from a heart rate sensor; and
determining information about the distance traveled based on the heart rate.

28. The machine-accessible storage medium of claim 27, wherein determining information comprises determining an incline, and adjusting the stride length to gait characteristic correlation based on the incline using an incline adjustment factor.

29. The machine-accessible storage medium of claim 20, the method further comprising:
comparing the distance traveled and the speed of travel to stored race data to generate a comparison result; and
presenting a real time performance indication that includes the comparison result.

30. The machine-accessible storage medium of claim 29, the method further comprising:
receiving the stored race data from one of a server and a mobile device.

31. The machine-accessible storage medium of claim 29, the method further comprising:
normalizing at least one of the distance traveled, the speed of travel, the stored distance traveled, and the stored speed of travel before comparing.

* * * * *